US009268777B2

(12) United States Patent
Lu et al.

(10) Patent No.: US 9,268,777 B2
(45) Date of Patent: *Feb. 23, 2016

(54) METHODS AND APPARATUS FOR DATA COLLECTION

(75) Inventors: Ligang Lu, New City, NY (US); Michael Peter Perrone, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 708 days.

This patent is subject to a terminal disclaimer.

(21) Appl. No.: 13/557,633

(22) Filed: Jul. 25, 2012

(65) Prior Publication Data

US 2013/0346359 A1    Dec. 26, 2013

Related U.S. Application Data

(63) Continuation of application No. 13/531,887, filed on Jun. 25, 2012.

(51) Int. Cl.
*G06F 17/30* (2006.01)
*G06F 19/00* (2011.01)
*G01V 1/00* (2006.01)
*G01V 1/38* (2006.01)

(52) U.S. Cl.
CPC .... *G06F 17/30067* (2013.01); *G06F 17/30286* (2013.01); *G06F 17/30592* (2013.01); *G06F 17/30595* (2013.01); *G01V 1/003* (2013.01); *G01V 1/3808* (2013.01); *G01V 2200/14* (2013.01); *G01V 2210/667* (2013.01); *G06F 19/3437* (2013.01)

(58) Field of Classification Search
CPC .................... G06F 17/30286; G06F 17/30067; G06F 17/30592; G06F 17/30595; G06F 7/122; G06F 19/3437

USPC ........................................ 707/600, 802; 703/6
See application file for complete search history.

(56) References Cited

U.S. PATENT DOCUMENTS 6,947,876 B1 * 9/2005 Galarza ................. G05B 17/02
                                                                        703/2
2010/0017138 A1    1/2010 Brady et al.
(Continued)

FOREIGN PATENT DOCUMENTS

WO    2009062935 A1    5/2009
WO    2010053733 A2    5/2010

OTHER PUBLICATIONS

Riahi et al., "A Statistical Strategy to Analyzing Passive Seismic Attributes", 73rd EAGE Conference & Exhibition incorporating SPE EUROPEC 2011, Vienna, Austria, May 23-26, 2011.

*Primary Examiner* — Shahid Alam
(74) *Attorney, Agent, or Firm* — Harrington & Smith

(57) ABSTRACT

Systems and techniques for directing data collection. Upon an initial data collection, the uncertainty of all or of a portion or portions of the collected data is evaluated. The collected data may be associated with a region, with portions of the collected data associated with subregions. Further data collection, including changes to or refinement of collection techniques, is undertaken based on evaluations of the uncertainty. Further data collection may be undertaken only for portions of the data for which uncertainty exceeds a threshold. Uncertainty evaluation may be performed at least in part using a model. The model may be an initial hypothesis model, and the model may be optimized as further data is collected, and the optimized model may be used to guide further data collection techniques, with iterations of data collection and model optimization being carried out concurrently.

20 Claims, 8 Drawing Sheets

(56) References Cited

U.S. PATENT DOCUMENTS

| | | |
|---|---|---|
| 2010/0118650 A1 | 5/2010 | Eick et al. |
| 2010/0177595 A1 | 7/2010 | Khare et al. |
| 2010/0212909 A1 | 8/2010 | Baumstein et al. |
| 2011/0066570 A1* | 3/2011 | Kolo et al. .................. 705/36 R |
| 2012/0123981 A1* | 5/2012 | Graves .............. G06F 17/30339 706/13 |

* cited by examiner

METHODS AND APPARATUS FOR DATA COLLECTION

CROSS-REFERENCE TO RELATED APPLICATIONS

The present application is a continuation of U.S. patent Ser. No. 13/531,887, filed on 25 Jun. 2012.

FIELD OF THE INVENTION

One or more embodiments of the present invention relate generally to systems and techniques for data collection. More particular, embodiments of the invention relate to directing data collection based at least in part on evaluations of the uncertainty associated with different portions of collected data.

BACKGROUND

Many activities depend on the collection of large and complex bodies of data. The data is processed and results of the processing are used to guide the activities. The collection of data in connection with many of these activities is itself complex and expensive. In one example, undersea oil drilling requires the collection of data to identify likely locations for oil deposits, because undersea drilling is enormously expensive. Energy concerns collect seismic data, which is then processed to identify locations of prospective deposits. One common data collection method is the towing of a hydrophone array by a ship. A ship may tow a two-dimensional array of hydrophones spaced approximately 25 meters apart on 1 to 16 trailed streamers. Every 15 seconds or so, an air cannon is fired into the water, creating an acoustic wave that propagates through the water and into the earth. Reflections from various surface and subsurface boundaries cause echoes that reflect back, and the echoes captured by each hydrophone in the array are recorded. The recording of a single hydrophone over time appears as a trace, and the collection of traces for a single firing of a cannon is called a common shot gather, or shot. As a ship moves, a large set of spatially overlapping shots is recorded. Depending on the survey region to be imaged, such data collection may take a month or more and is designed to achieve maximal coverage of an area to be imaged. Usually a ship passes back and forth over an area at a slow speed, performing tens of thousands of shots. A data collection ship may cost on the order of $1 million per day.

SUMMARY

In one embodiment of the invention, an apparatus comprises at least one processor and memory storing computer program code. Execution of the computer program code by a processor causes the apparatus to perform actions comprising at least evaluating uncertainty associated with at least one subset of a set of collected data, and, if the at least one subset of the set of collected data is characterized by uncertainty exceeding a specified threshold, directing additional data collection to refine the at least one subset of the set of data.

In another embodiment of the invention, a method comprises evaluating uncertainty associated with at least one subset of a set of collected data, and, if the at least one subset of the set of collected data is characterized by uncertainty exceeding a specified threshold, directing additional data collection to refine the at least one subset of the set of data.

In another embodiment of the invention, a computer readable medium stores computer program code. Execution of the computer program code by a processor configures an apparatus to perform actions comprising at least evaluating uncertainty associated with at least one subset of a set of collected data, and, if the at least one subset of the set of collected data is characterized by uncertainty exceeding a specified threshold, directing additional data collection to refine the at least one subset of the set of data.

DETAILED DESCRIPTION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the present invention recognize that the typical area over which data is collected using mechanism such as those described above is not uniform, and in cases of oil exploration, areas rich in oil deposits tend to be more complex. Therefore, the areas of most interest are more complex and tend to require the most data gathering, while simpler areas also tend to be areas of less interest. In addition, simpler areas inherently require less data gathering than do complex areas. A uniform survey of areas of varying complexity will therefore cause needless expense for surveying of simple areas, or insufficient data gathering for surveying of complex areas. Embodiments of the present invention therefore use evaluations of uncertainty in the data that has been gathered to determine the regions for which additional data gathering needs to be performed. Embodiments of the invention also provide users with information that allows them to determine the areas in which sufficient data collection has been performed and the areas in which additional data collection needs to be performed. Embodiments of the invention also allow users to direct additional data collection in areas in which such collection should be performed.

Figure 1:
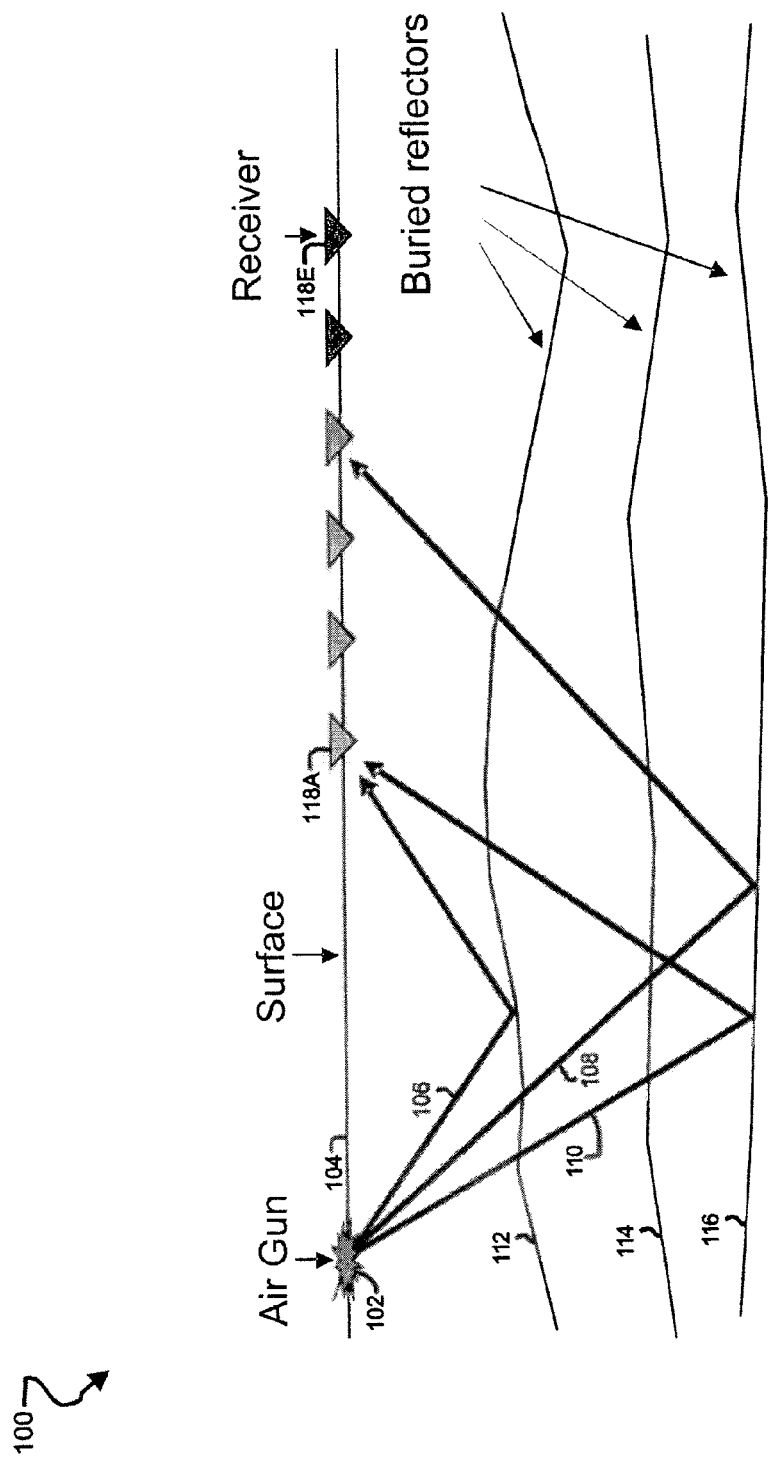
FIGS. 1 and 2 illustrate mechanisms for data collection that can be directed using one or more embodiments of the present invention.

FIG. 1 illustrates a mechanism 100 for data collection that may be directed according to one or more embodiments of the present invention. A discharge 102 of an air cannon into a body of water creates acoustic waves, here illustrated as 106, 108, and 110, that bounce off reflective surfaces 112, 114, and 116 and are captured by receivers 118A, . . . , 118E. The acoustic waves captured by the receivers, such as hydrophones, are processed to provide images of the reflective surfaces, which are or provide insight into, geological features beneath the surface of the soil, which in turn lies beneath the water.

Figure 2:
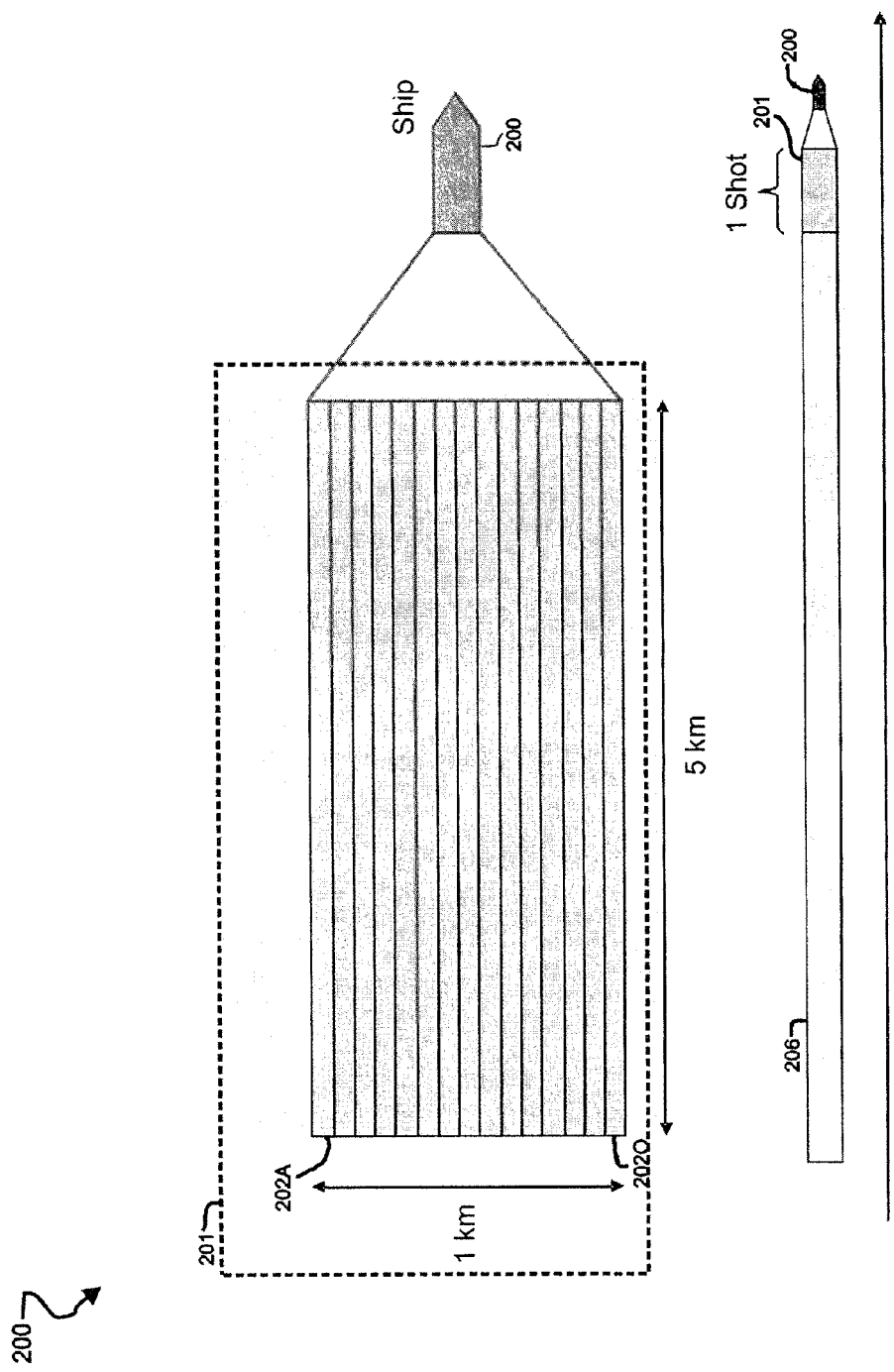

FIG. 2 illustrates a ship 200 that tows an array 201 of streamers 202A, . . . , 202O, with each of the streamers comprising a set of hydrophones spaced apart, at a separation of approximately 25 meters. The array may be on the order of 5 km long and 1 km across, and the assembly is towed over an area of interest. As noted above, a great deal of data needs to be collected, requiring many shots and many passes over the area of interest, to provide reliable data for oil exploration. One or more embodiments of the present invention direct the collection of data by taking data from an initial pass or set of passes, analyzing the data in terms of uncertainty, and directing further passes, which may be modified as needed, over areas exhibiting uncertainty. The new data is further analyzed and further additional passes may be made, until a sufficient level of certainty is achieved. FIG. 2 further illustrates a more distant view of the ship 200 and the array 201 as the ship tows the array 201 along a path 206.

Figure 3:
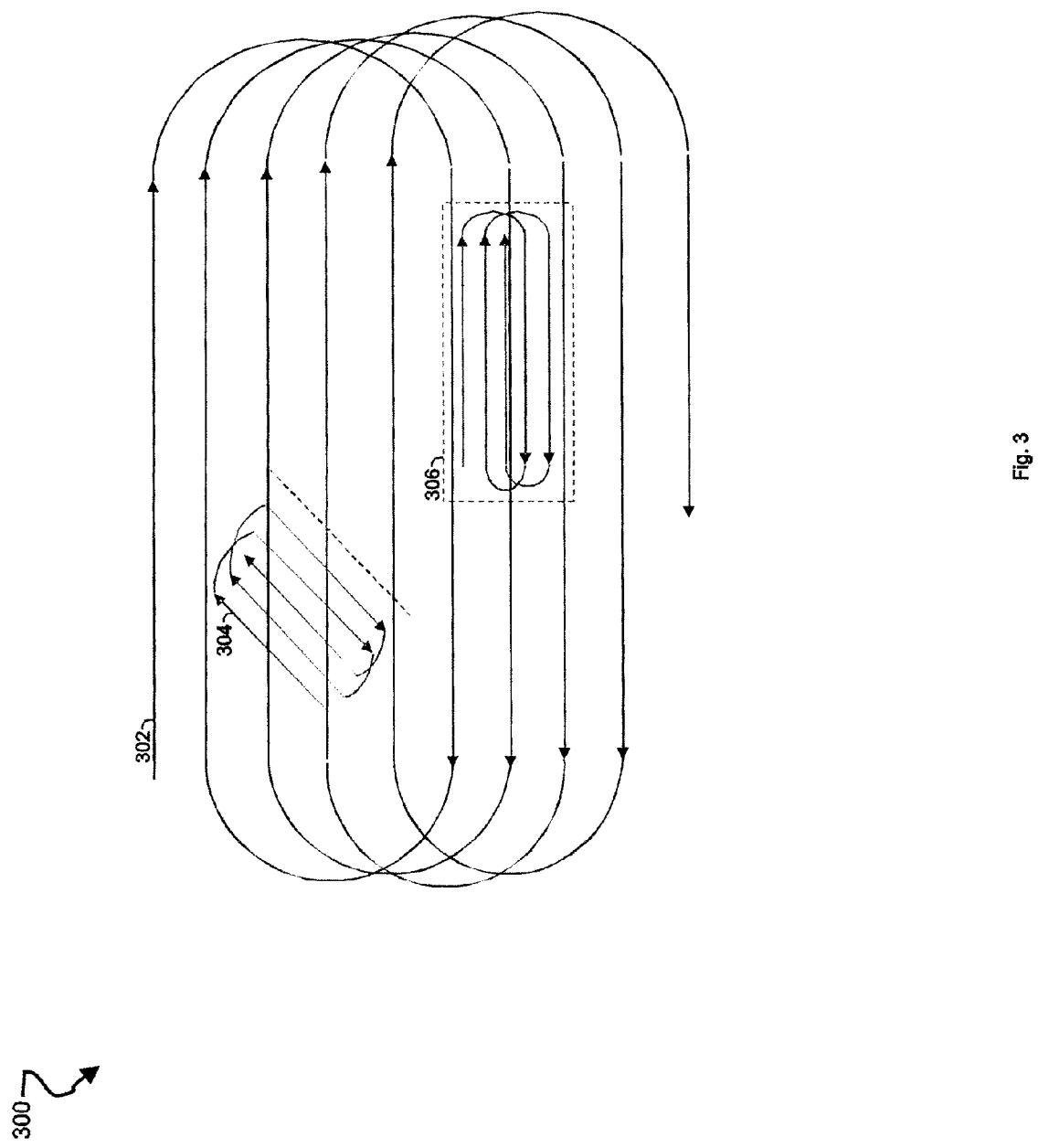
FIG. 3 illustrates a procedure for data collection according to an embodiment of the present invention.

FIG. 3 illustrates an exemplary search pattern 300 that may be achieved using one or more embodiments of the present invention. An initial pattern 302 is performed, using relatively wide spacing, to collect an initial set of data. The initial pattern 302 may cover both simple and complex areas (whose relative simplicity and complexity are typically not known, or not well known, before the initial search takes place). The initial set of data is processed, with the processing typically including imaging. The processing and imaging may use one or more models whose general structure may be known in the applicable art, such as oil exploration, reservoir modeling, structure damage detection, and the like, and the one or more models may be refined as needed using one or more embodiments of the present invention. The models are used to direct the data collection and the data is in turn used to enhance the models, with each of the data collection and the modeling being improved by the other.

Figure 4:
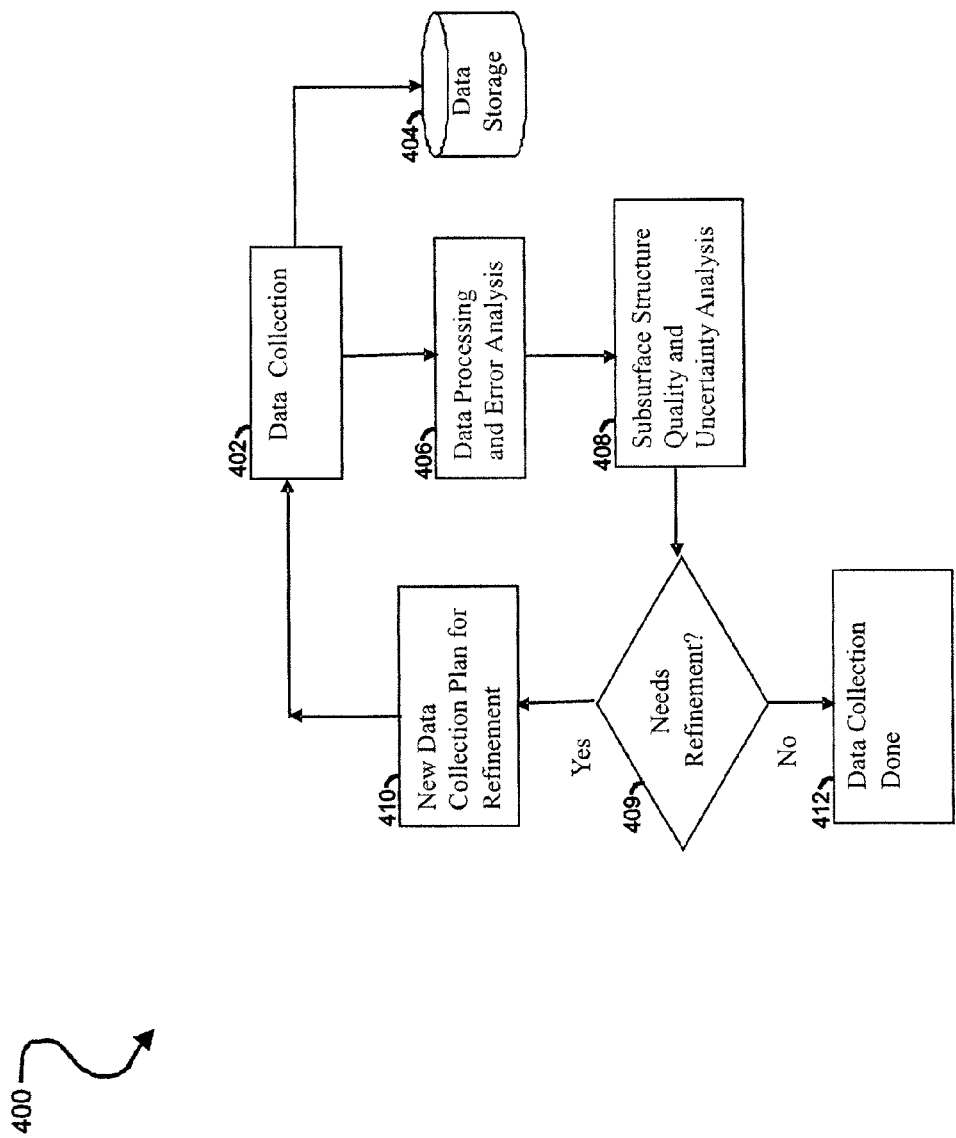
FIG. 4 illustrates a process for directing data collection according to an embodiment of the present invention.

FIG. 4 illustrates a process 400 of data collection according to an embodiment of the present invention. The exemplary process 400 described here relates to data relating to subsurface structure information, but it will be recognized that embodiments of the present invention may be used in connection with any number of data collection operations in which the uncertainty of data that is gathered can influence data gathering techniques. During the data collection process 400, a complete simulation is performed with a hypothesis model, carrying out a forward acoustic wave propagation pass to generate simulated trace data. Sensitivity analysis and error minimization are performed, and model parameters may be adjusted to minimize an error between collected data and simulated data. A separate model optimization process, illustrated in FIG. 7 and discussed in greater detail below, may be performed.

At 402, data collection is performed, and the data is stored in data storage 404. At step 406, data processing and error analysis are performed. At step 408, subsurface structure quality and uncertainty analysis are performed. An evaluation is performed at step 409 to determine if refinement of the data is needed. If refinement of the data is needed, the process proceeds to step 410 and a new data collection plan to achieve the refinement is generated. The data collection plan may, for example, designate areas in which more detailed surveying is to be performed and may specify various techniques to be used. In cases in which acoustic wave collection is to be performed, the data collection plan may designate changes such as increased shot frequency, higher data sampling rates, new angles for positioning of the cannon so as to collect data from waves penetrating the surface at different angles, and so on. The data collection plan may also specify the density of a pattern of passes, the number and direction of passes, and any other relevant information.

The process then returns to step 402 and additional data collection is performed according to the new data collection plan. The data is again analyzed and if refinement is needed, a further new data plan is created and further data collection is performed. When no refinement is needed, either after initial data collection and analysis, or after a later iteration, the process ends at step 412.

Figure 5:
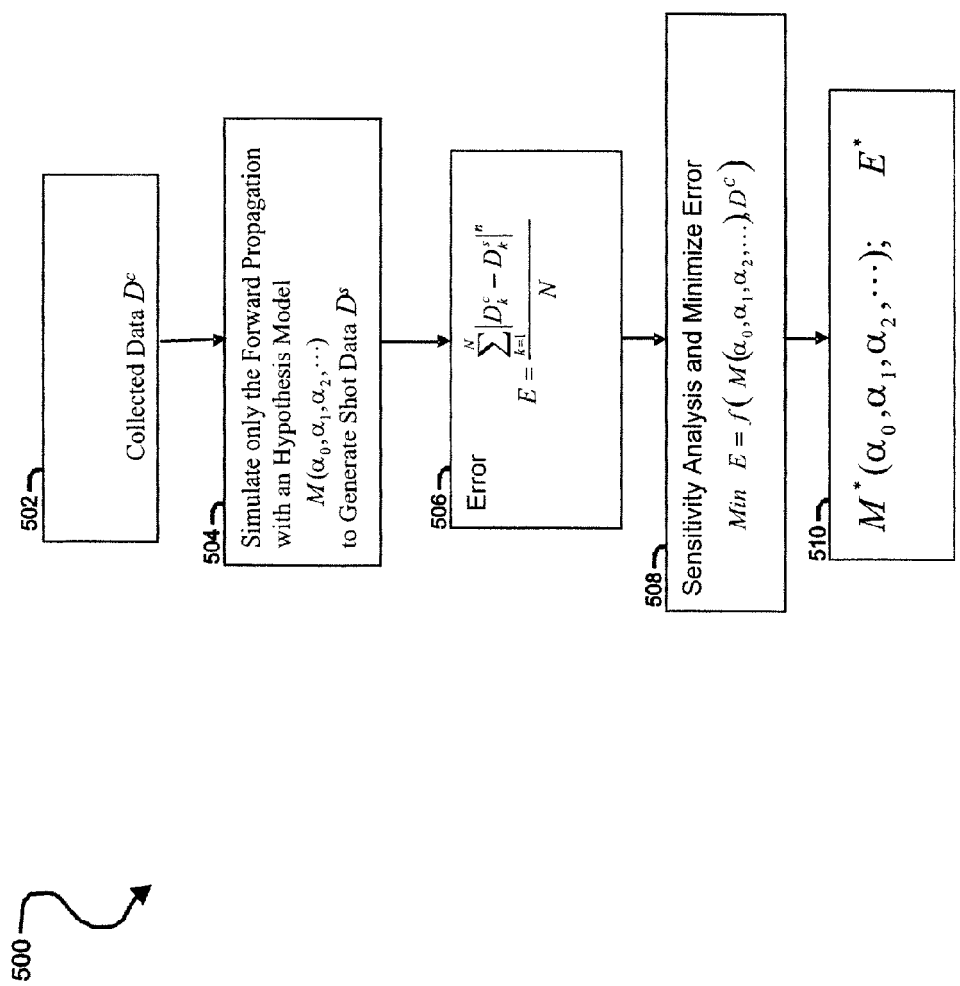
FIGS. 5 and 6 illustrate additional details of directing data collection according to an embodiment of the present invention

Additional details of the data processing and error analysis performed at step 406, and the subsurface structure quality and uncertainty analysis performed at step 408, are presented at FIGS. 5 and 6, respectively, and discussed below. FIG. 5 illustrates a process 500 that may be performed at step 406 of the process 400 of FIG. 4. At step 502, collected data $D^c$ is retrieved from data storage 404. At step 504, the forward propagation portion of the data is simulated with a hypothesis model $M(\alpha_0, \alpha_1, \alpha_2, \ldots)$ to generate shot data $D^s$. At step 506, an error value is computed for the set of data by comparing the collected data with the model, using the formula $$E = \frac{\sum_{k=1}^{N} |D_k^c - D_k^s|^n}{N}.$$

At step 508, a sensitivity analysis and error minimization Min $E=f(M(\alpha_0, \alpha_1, \alpha_2, \ldots), D^C)$ is performed to yield model parameters that minimize the error: $M^*(\alpha_0, \alpha_1, \alpha_2, \ldots); E^*$. These model parameters are then used to perform subsurface quality and uncertainty analysis.

Figure 6:
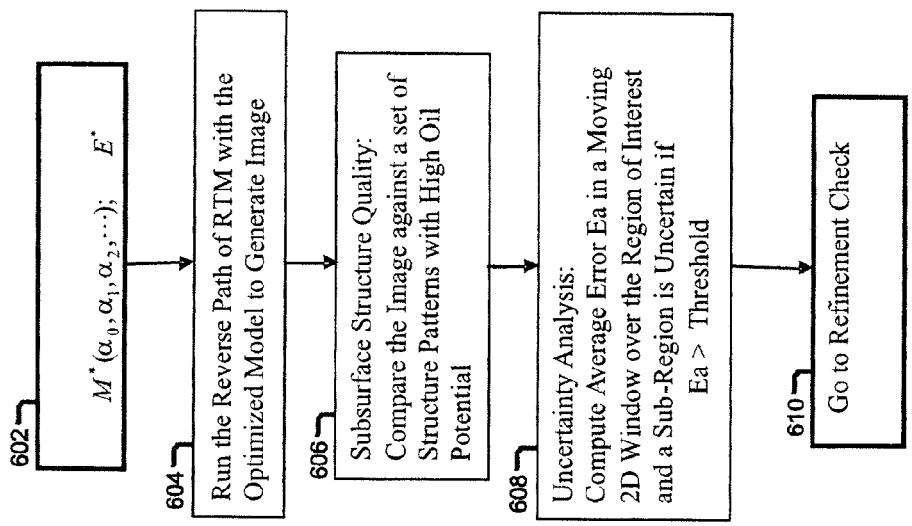
Figure 7:
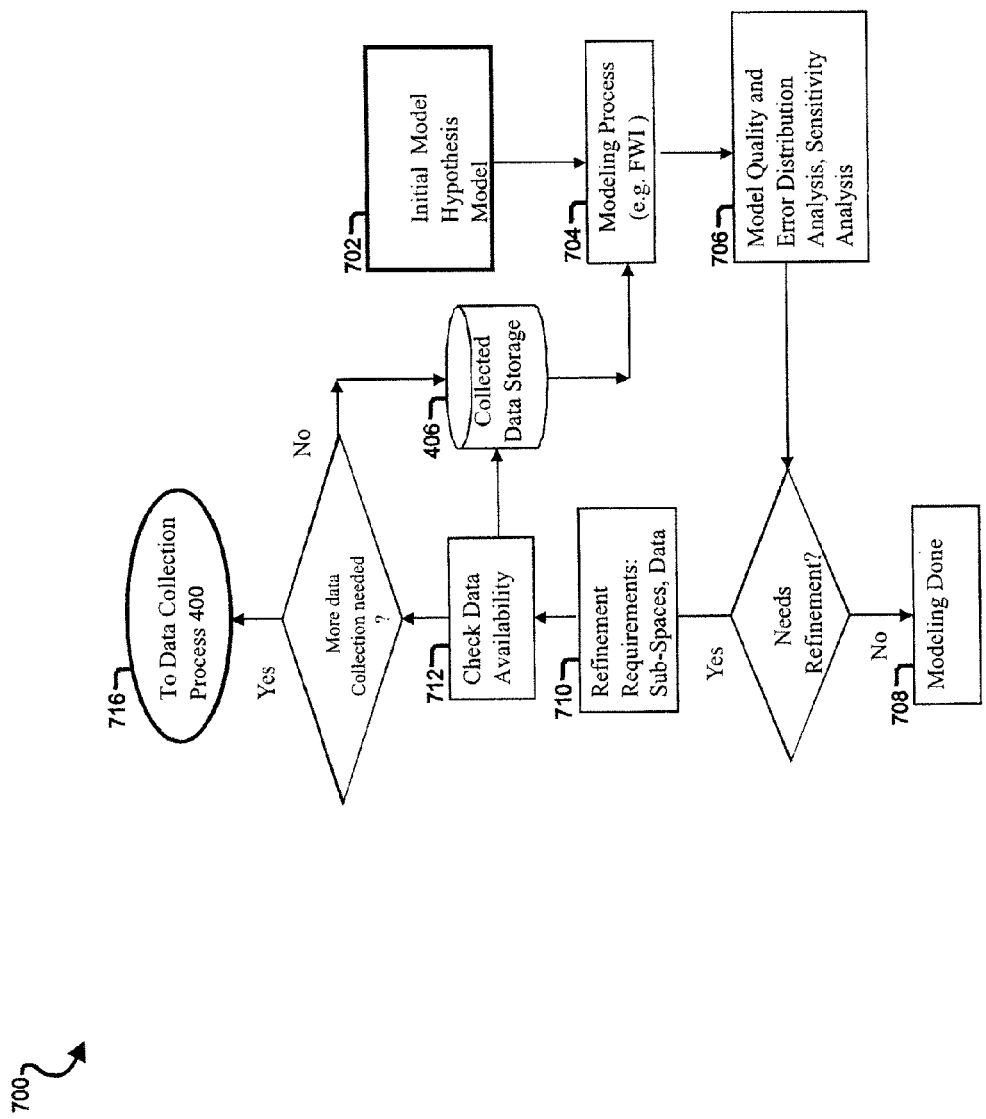
FIG. 7 illustrates a process of model optimization according to an embodiment of the present invention.

FIG. 6 illustrates a process 600 of subsurface quality and uncertainty analysis according to an embodiment of the present invention. At step 602, the sensitivity and error values generated by the process 500 are received. At step 604, a reverse path of reverse time migration (RTM) is processed with a current model to generate an image. The model may be iteratively optimized along with the data collection process, as illustrated at FIG. 7 and described in additional detail below. At step 606, subsurface structure quality analysis is performed. In one exemplary case in which embodiments of the invention may be used, the image is compared against a set of structure patterns associated with a high likelihood for the presence of oil. If it can be clearly established that the region does not have high oil potential, the analysis can be ended, but if the region, or a portion of the region, has high oil potential, an uncertainty analysis is performed at step 608. One exemplary mechanism for the uncertainty analysis is to compute an average error $E_a$ in a moving window, such as a two-dimensional window, over a region of interest. The window may move in increments with each incremental movement of the window defining a subregion. A subregion is uncertain if the value of $E_a$ exceeds a threshold. For each image, an error measure may be calculated between measured seismic data and data generated by the model by "shooting" the model using techniques familiar to those skilled in the art. Error measures are then used to generate a probability associated with each model and the error measure is used to inform the data collection process as to which regions have low degrees of uncertainty or variability and which regions have high degrees of uncertainty or variability relating to subsurface structures of interest. At step 610, the results of the uncertainty analysis are used for the evaluation step 409 of FIG. 4.

The process 400 continues with the result of the uncertainty analysis, with a determination being made if further refinement of one or more subregions is needed, and if further refinement is needed, the process 400 proceeds as described above.

FIG. 7 illustrates a process 700 of model optimization according to one or more embodiments of the present invention. At step 702, an initial hypothetical model is specified. At step 704, a modeling process is performed, such as full waveform immersion (FWI), using stored data such as the data 404 of FIG. 4. At step 706, model quality and error distribution analysis and sensitivity analysis are performed. If the analysis indicates that the model does not need refinement, the process terminates at step 708. If the analysis indicates that the model needs refinement, the process proceeds to step 710 and refinement requirements are generated, such as requirements for subspaces and requirements relating to the data needed. The process then proceeds to step 712 and an evaluation is made as to whether sufficient data for further refinement is available. If no more data collection is needed, the process returns to step 704, repeating the modeling process with data available in data storage 406. If additional data collection is needed, the process proceeds to step 716 and additional data is collected using the process 400. The process 400 need not be completed before data collected by the process is used. Instead, new data may be collected and the data used to refine the model, with the refined model being used in turn, with refined data being used at successive iterations of the process 700 and refined models being used at successive iterations of the process 400. Such successive iterations may be continued with one process terminating when its goal is met. The goals of each of the processes 400 and 700 may be influenced by the needs of the other process, so that each process may continue as long as it can achieve improvements at a desired level of efficiency, so long as those improvements can benefit the other process.

Figure 8:
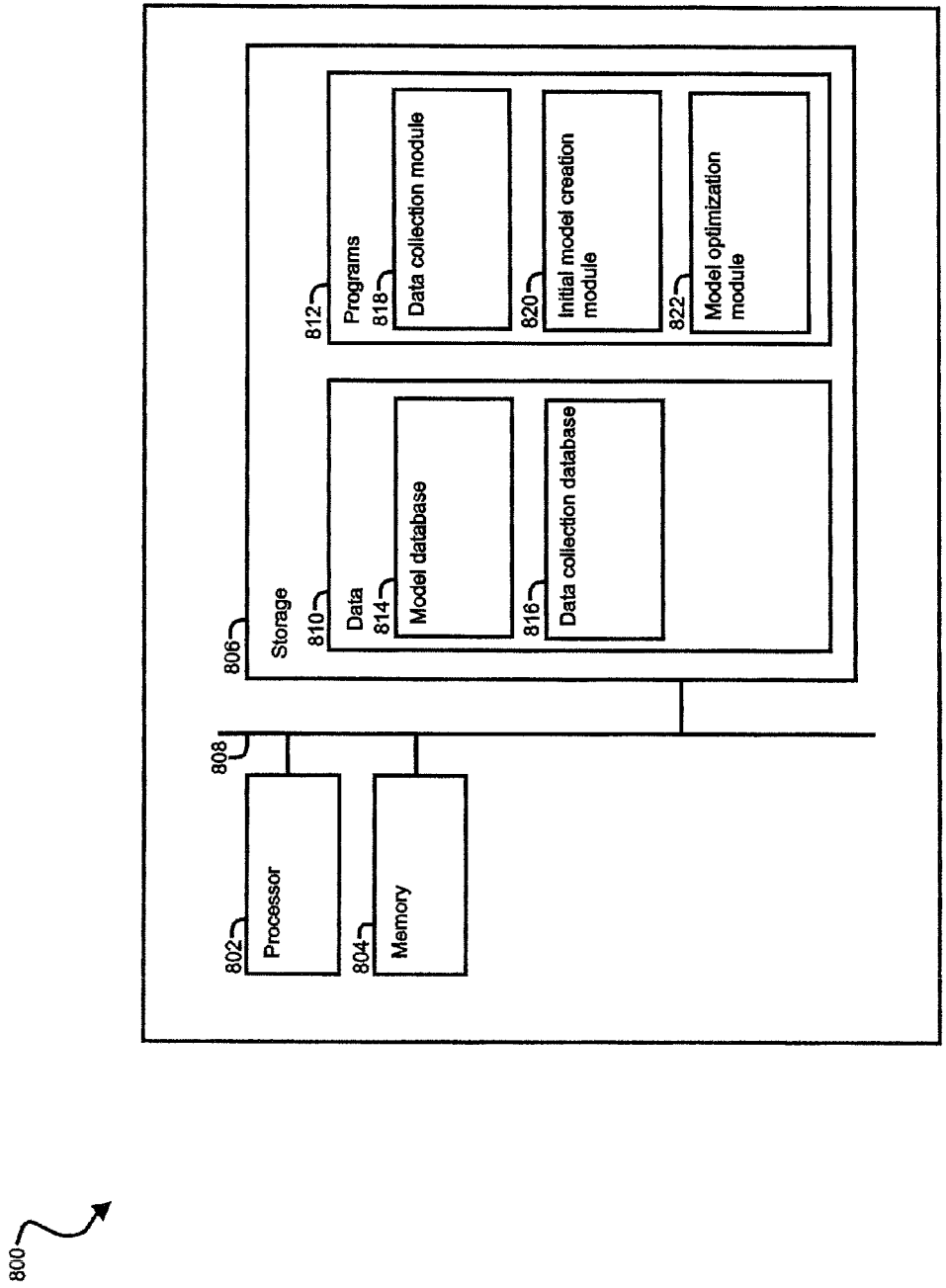
FIG. 8 illustrates a system for directing data collection according to an embodiment of the present invention.

FIG. 8 illustrates a data processing system 800 that may be used to carry out one or more embodiments of the present invention. The system 800 comprises a processor 802, memory 804, and storage 806, communicating over a bus 808. The system 800 may employ data 810 and programs 812, residing in storage 806 and transferred to memory 804 as needed for execution by the processor 802. Included in the data 810 may be a model database 814, which may store one or more initial models and subsequent refinements of the model or models. Also included in the data 810 may be a data collection database 816 for receiving and storing collected data and a comparison database storing data relating to characteristics of interest against which collected data may be compared. Included in the programs 812 may be a data collection module 818, an initial model creation module 820, and a model optimization module 822. The various modules 816, 818, and 820 may cause the carrying out of operations such as those described above in relation to the processes 400, 500, 600, and 700 of FIGS. 4-7, respectively.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, or the like, or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Various embodiments of the present invention improve over conventional techniques by directing data collection using an evaluation of uncertainty associated with already collected data. An initial less detailed collection may be performed over a large region, and this less detailed collection need not be refined for subregions for which the uncertainty is sufficiently low. For subregions for which the data exhibits a higher uncertainty, further or refined data collection can be performed. A model may be used to determine the uncertainty, with an initial hypothesis model being used at first, and with this model being iteratively optimized using refined data as further refinements to data collection are made. In turn, further refinements to data collection may be made based on the optimized model.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

We claim:

1. An apparatus comprising:
   at least one processor;
   memory storing computer program code;
   wherein the memory storing the computer program code is configured to, with the at least one processor, configure the apparatus to at least:
   create a model using a set of collected data evaluate uncertainty associated with at least one subset of the set of collected data;
   if the at least one subset of the set of collected data is characterized by uncertainty exceeding a specified threshold, directing additional data collection to refine the at least one subset of the set of data;
   evaluate the model to determine if the model requires refinement; and
   iteratively refine the model using the additional data and directing additional data collection and refining the at least one subset of the set of data using the refined model.

2. The apparatus of claim 1, wherein the set of collected data comprises a result of an initial collection and is characterized by a relatively low level of detail.

3. The apparatus of claim 1, wherein evaluating uncertainty comprises performing quality and error distribution analysis for at least one subset of the set of collected data.

4. The apparatus of claim 3, wherein the set of collected data comprises data collected over a larger region and each of the subsets of collected data comprises data collected over a subregion of the larger region.

5. The apparatus of claim 1, wherein directing additional data collection comprises directing specified mechanisms of data collection.

6. The apparatus of claim 5, wherein at least one of the specified mechanisms of data collection comprises a higher density of data collection relative to the initial data collection.

7. The apparatus of claim 1, wherein evaluating uncertainty comprises:
   generating processed data using a model to process the collected data;
   computing an error for the processed data; and
   performing sensitivity analysis and error minimization for the processed data.

8. The apparatus of claim 7, wherein evaluating uncertainty further comprises iteratively optimizing the model as further data is collected.

9. The apparatus of claim 1, wherein evaluating uncertainty comprises comparing an error value against a threshold, and wherein a subset of data is designated as uncertain if its error value exceeds a threshold.

10. The apparatus of claim 9, wherein the error value is an average error value computed over a subset of data defined by a moving window.

11. An apparatus comprising:
    at least one processor:
    memory storing computer program code:
    wherein the memory storing the computer program code is configured to, with the at least one processor, cause the apparatus to at least:
    perform a modeling process using stored data;
    perform at least one of model quality analysis, error distribution analysis, and sensitivity analysis;
    determine, based at least in part on the at least one of the model quality analysis, error distribution analysis, and sensitivity analysis, if the model requires refinement; and
    iteratively refine the model, wherein refining the model comprises collecting and storing additional data, and wherein collection and storage of additional data is also iteratively performed, with collection and storage of additional data being refined as the model is refined, with additional and refined data being used to refine the model and with the refined model being used to direct collection of additional data and to refine the data.

12. The apparatus of claim 11, wherein refining the model continues until a specified level goal is met.

13. The method of claim 11, wherein refining the model continues so long as improvements can be achieved at a desired level of efficiency.

14. The method of claim 11, wherein the modeling process is a full waveform immersion process.

15. A non-transitory computer readable medium storing a program of instructions, execution of which by a processor configures an apparatus to at least:
    create a model using a set of collected data
    evaluate uncertainty associated with at least one subset of the set of collected data;
    if the at least one subset of the set of collected data is characterized by uncertainty exceeding a specified threshold, directing additional data collection to refine the at least one subset of the set of data;
    evaluate the model to determine if the model requires refinement; and
    iteratively refine the model using the additional data and directing additional data collection and refining the at least one subset of the set of data using the refined model.

16. The non-transitory computer readable medium of claim 15, wherein the set of collected data comprises a result of an initial collection and is characterized by a relatively low level of detail.

17. The non-transitory computer readable medium of claim 15, wherein evaluating uncertainty comprises performing quality and error distribution analysis for at least one subset of the set of collected data.

18. The non-transitory computer readable medium of claim 17, wherein the set of collected data comprises data collected over a larger region and each of the subsets of collected data comprises data collected over a subregion of the larger region.

19. The non-transitory computer readable medium of claim 15, wherein directing additional data collection comprises directing specified mechanisms of data collection.

20. The non-transitory computer readable medium of claim 18, wherein at least one of the specified mechanisms of data collection comprises a higher density of data collection relative to the initial data collection.

* * * * *